| United States Patent [19] | [11] Patent Number: 4,773,933 |
| Futami et al. | [45] Date of Patent: Sep. 27, 1988 |

[54] ZINC OXIDE EUGENOL CEMENT COMPOSITIONS FOR DENTAL PURPOSES

[75] Inventors: Shunichi Futami, Nagareyama; Sueo Saito, Tokyo, both of Japan

[73] Assignee: G-C Dental Industrial Corp., Tokyo, Japan

[21] Appl. No.: 103,395

[22] Filed: Oct. 1, 1987

[30] Foreign Application Priority Data

Oct. 31, 1986 [JP] Japan .............................. 61-258481

[51] Int. Cl.$^4$ ................................................ C09K 3/00
[52] U.S. Cl. ...................................................... 106/35
[58] Field of Search ........................................... 106/35

[56] References Cited

U.S. PATENT DOCUMENTS 1,408,960  3/1922  Schiff ..................................... 106/35
1,886,982  11/1932  Simon .................................... 106/35
1,900,237  3/1933  Harshman ............................. 106/35

*Primary Examiner*—Theodore Morris
*Attorney, Agent, or Firm*—Oblon, Fisher, Spivak, McClelland & Maier

[57] ABSTRACT

A dental zinc oxide eugenol cement composition which is used in dentistry as the temporary sealing material having a anodyne, sedative and antiphlogistic effect upon oral disease and the temporary cementing material for restorations comprising in combination a putty-form base agent composition wherein 5.0 to 50.0% by weight of silicic acid are contained in an eugenol-containing base agent composition, and a putty-form setting agent composition wherein 0.5 to 15.0% by weight of an inorganic filler material which has a solubility of up to 0.2 g per 100 ml of water at 20° C. are contained in a zinc oxide-containing setting agent composition.

2 Claims, No Drawings

ZINC OXIDE EUGENOL CEMENT COMPOSITIONS FOR DENTAL PURPOSES

BACKGROUND OF THE INVENTION

1. Field of the Invention

The present invention relates to a zinc oxide eugenol cement composition which is used in dentistry as the temporary sealing material having an anodyne, sedative and antiphlogistic effect upon oral disease and the temporary cementing material for restorations such as clowns and bridges.

2. Statement of the Prior Art

The temporary sealing and cementing materials are indispensable for ordinary dentistry, and are used for the purpose of, e.g., temporary sealing for the sedation of cavities after the elimination of dental caries, temporary cementing of temporary crowns after pier tooth preparation, and temporary sealing for medicaments in endodontics. The temporary sealing material is generally classified into the following three types.

(1) Temporary stopping composed mainly of gutta-percha,
(2) Hydraulic temporary sealing material, and
(3) Zinc oxide eugenol cement.

The temporary stopping is thermoplastic, and is put on the market in the bar or pellet form. In use, this is softened by heating, and is pressed in a tooth cavity for temporary sealing. Due to its simplicity, such a stopping method has been used for many years. With this material, however, there is left much to be desired in view of the marginal sealing effect, since it shrinks largely when cooled and set, so that its adherence to a tooth is insufficient.

The hydraulic temporary sealing material also leaves much to be desired in view of the marginal sealing effect, since it takes a long period of time (several hours) for setting, and produces only an insufficient bonding strength to a tooth.

The requirements of the temporary sealing material are that:

(1) it has a good marginal sealing effect upon the margin of a cavity,
(2) it is easily removable in detachment, and
(3) it set within a short time.

Since the zinc oxide eugenol cement meets all the requirements, excels in flowability, and has suitable degrees of strength and bonding strength, it is frequently used as the temporary cementing material. The zinc oxide eugenol cement is supplied in the form of (1) a combination of a powdery setting agent containing zinc oxide with a liquid base agent containing eugenol, and (2) a combination of a tube in which a setting agent containing zinc oxide in a highly flowable pasty state with a tube in which a base agent containing eugenol in a highly flowable pasty state.

In use, the setting and base agents are mixed together for temporary sealing or cementing use. Such mixing are mainly carried out by a dental assistant.

The time needed to finish mixing of the setting and base agents varies depending upon the skill of operators, and has a great influence upon the performance of the set product, since there is a difference in the dispersed state between both agents. Especially when mixing a liquid base agent containing eugenol with a powdery setting agent containing zinc oxide, the powdery component is divided into three equal portions which are to be successively mixed with the liquid component to the desired consistency. Since the powders scatter vigorously, however, difficulty is encountered in the incorporation thereof into the liquid component, and a relatively long time of 1 to 2 minutes is required for mixing. Depending upon mixing skill, there are differences in the dispersed state achieved by mixing and in the time needed to finish mixing, which have a remarkable influence upon the workability of temporary sealing and cementing and the bonding strength. Thus, the zinc oxide eugenol cement is a material-difficult-to-handle, for which a dental assistant or hygienist in charge of mixing is required to have skill. If the eugenol-containing base agent and the zinc oxide-containing setting agent each are in the form of a highly flowable paste, it is then relatively easy to force that paste out of the tube by equal length onto a mixing pad for mixing. However, it is likely that such a paste may leak out of the tube in use or storage and pollute a clinic room, giving out a strongly irritating eugenol odor. Thus, the zinc oxide eugenol cement is a material which is difficult for an operator to handle. The set product is also relatively soft so that it wears away due to biting or brushing, thus offering a deformation or disengagement problem.

As mentioned above, as long as the zinc oxide-containing setting agent and the eugenol-containing base agent are used in the powder-to-liquid form or paste-to-paste form, as is the case with the prior art, difficulty would be still encountered in mixing thereof, and a leakage problem difficult to solve would be likely to arise in use and storage.

SUMMARY OF THE INVENTION

An object of the present invention is to provide a zinc oxide eugenol cement composition comprising a putty-form setting agent and a putty-form base agent, which can easily be available by the desired amount with the use of a spatula, and which can be so easily mixed together by anyone regardless of skillfulness and within a short period of time and assure comfortable diagnosis and treatment activities, since any leakage problem does not arise in use and storage.

According to the present invention, this object is achieved by the provision of a zinc oxide eugenol cement based on the aforesaid liquid-to-powder and paste-to-paste types having improved abrasion resistance and hence high durability, in which silicic acid is added to and mixed with a base agent composition containing eugenol, and an inorganic filler material having a solubility of up to 0.2 g per 100 ml of water at 20° C. (which may hereinafter be simply referred to as the inorganic filler material) is added to and mixed with a setting agent composition containing zinc oxide. It is to be appreciated that, in the aforesaid liquid-to-powder type zinc oxide eugenol cement, vegetable oils and so on may be added, when making the powdery setting agent composition putty.

EXPLANATION OF SOME PREFERRED EMBODIMENTS OF THE INVENTION

The wordings "setting agent and base agent made putty" or "putty-form setting agent and base agent" used in this disclosure refer to those showing a deformation of natural fluidity of within 10% (a diameter of 11 mm) with respect to the original diameter, when extruding a sample onto a flat plate with an applicator (of 10 mm in diameter and 0.5 ml in volume) used to measure the consistency of dental zinc phosphate cement according to JIS T 6602 and measuring its diameter after the lapse of 30 seconds.

By making the setting and base agents putty, there is no likelihood that the material may flow out of a package. Nor does any leakage of the material occur at all during use or storage. Thus, it is possible to reduce the emission of an eugenol odor to such a low level that comfortable diagnosis and treatment activities are sufficiently expected.

The abrasion resistance of the set product has also been found to be improved by adding silicic acid to the base agent and incorporating into the setting agent an inorganic filler material having a solubility of up to 0.2 g per 100 ml of water at 20° C. (which may hereinafter be simply referred to as the inorganic filler).

The zinc oxide eugenol cement undergoes a promoted setting reaction in the presence of water and an acid, in which reaction the zinc oxide is chelated with the eugenol for setting.

In the zinc oxide eugenol cement of the present invention, it is unsuitable to use the setting agent containing zinc oxide with the inorganic filler material having a solubility exceeding 0.2 g per 100 ml of water at 20° C., since the temporarily sealed set product is then likely to be dissolved and disintegrated. It is unsuitable neither to incorporate into the base agent any carbonate, metal oxide and hydroxide, silicate and barium sulfate, partly because some internal reaction may possibly be caused, and partly because the agent may lose transparency and be even clouded, thus resulting in settlement and separation. Still further, unsuitable for the present invention are diatomeceous earth owing to its coarseness leading to considerable coarsening of the set product and an organic filler material due to the fact that it reduces the strength of the set product and is not particulate. In the present invention, therefore, the base and setting agents are suitably pasted by permitting the eugenol-containing base agent to contain silicic acid and the zinc oxide-containing setting agent to contain the inorganic filler material having a solubility of up to 0.2 g per 100 ml of water at 20° C. Finely divided silicic acid is broken down into the anhydrous type (having a water of crystallization plus bound water content of below 5%) and the hydrous type (having a water of crystallization plus bound water content of 5% or more), which may be added to the eugenol-containing base agent alone or in combination. It is to be understood that the fine powders of such silicic acids may previously be alkylated and rendered hydrophobic on the surfaces with a silane coupling agent such as chlorosilane having an alkyl group and a methoxysilane having an alkyl group. The inorganic filler materials having a solubility of up to 0.2 g per 100 ml of water at 20° C. include anhydrous silicic acid, hydrous silicic acid, aluminium oxide, titanium oxide, calcium oxide, zirconium oxide, magnesium oxide, aluminium hydroxide, calcium hydroxide, magnesium hydroxide, aluminium silicate, calcium silicate, zirconium silicate, magnesium silicate and barium sulfate, which may be added to the zinc oxide-containing setting agent alone or in admixtures of two or more thereof.

In the zinc oxide eugenol cement, it is required that the silicic acid and inorganic filler used be within a suitable range of particle sizes for the purpose of easily obtaining and mixing a sample from the putty-form base and setting agents. More specifically, when preparing the putty-form zinc oxide eugenol cement with silicic acid and the inorganic filler, each having a mean particle size of below 2 millimicrons, it tends to adhere easily to a spatula in obtaining or mixing the base and setting agents, and the resulting mixture tends to adhere easily to hands, fingers and applicators, thus offering a handling problem. For that reason, the lower limit particle sizes of the silicic acid and inorganic filler to be used in the present invention should be limited to 2 millimicrons. When preparing the putty-form zinc oxide eugenol cement with silicic acid and the inorganic filler, each having a particle size exceeding 2000 millimicrons, the mixed product becomes rough. Thus, the surface of the set product, temporarily sealed in place, becomes so coarse that foreign matters may easily be deposited thereon. When the cement is used for temporary cementing, on the other hand, it shows unsatisfactory flowability upon cementing of an temporary crown, and provided a thick film, thus making occlusal adjusting difficult. Accordingly, the upper limit of the particle sizes of the silicic acid and inorganic filler is limited to 2000 millimicrons.

In the dental zinc oxide eugenol cement, the proportion of the silicic acid to be mixed should be at least 5.0% by weight so as to make putty the eugenol-containing base agent and thereby make it easy to obtain it by means of a spatula. On the other hand, the proportion of the silicic acid to be mixed should be at most 50.0% by weight to maintain its own function without deteriorating its original physical properties. In order to make putty the zinc oxide-containing setting agent to reduce its viscous property and thereby making it easy to obtain it by means of a spatula, the proportion of the inorganic filler to be mixed should be at least 0.5% by weight. The upper limit of the proportion of the inorganic filler to be mixed, on the other hand, should be at most 15.0% by weight so as to maintain its own function without deteriorating its original physical properties.

Thus, (A) the proportion of the finely divided silicic acid to be mixed with the eugenol-containing base agent composition is limited to a range of 5.0 to 50.0% by weight, preferably 18.0 to 35.0% by weight, and (B) the proportion of the inorganic filler, having a solubility of up to 0.2 g per 100 ml of water at 20° C., to be mixed with the zinc oxide-containing setting agent composition is restricted to a range of 0.5 to 15% by weight, preferably 2.0 to 8.0% by weight.

Eugenol is the main component of clove oil, and is contained therein in an amount of 80% or higher. In general, clove oil is used as eugenol.

The known zinc oxide eugenol cement compositions used in the present invention comprise the eugenol-containing base agent compositions and the zinc oxide-containing setting agent compositions. The base agent composition are mixed with the setting agent compositions, whereby the eugenol is chelated with the zinc oxide for setting. Known additives such as rosin, rosin derivatives, zinc acetate, glacial acetic acid, acetic acid, vegetable oils, coloring agents, perfumes and so on may optionally be added to both base agent compositions and setting agent compositions. Typical examples of the known zinc oxide eugenol cement compositions are given below.

(1) Zinc Oxide Eugenol Cement (of the Liquid-Powder Type)
  (a) Base Agent (Liquid) Component
    Clove Oil
  (b) Setting Agent (Powder) Component
    Zinc Oxide, Rosin and Zinc Acetate If required, coloring matters, perfumes and so on may be used.
(2) Zinc Oxide Eugenol Cement (of the Paste-Paste Type)
  (a) Base Agent (Paste) Component
    Clove Oil, Rosin and Glacial Acetic Acid or Acetic Acid
  (b) Setting Agent (Paste) Component
    Zinc Oxide and Vegetable Oils
If required, coloring matters, perfumes and so on may be used.

The present invention will now be explained, particularly but not exclusively, with reference to the following examples.

EXAMPLE 1

(a) Base agent

| | |
|---|---|
| Clove oil | 51 |
| Hydrous silicic acid having a mean particle size of 16 millimicrons (manufactured by Nippon Silica, Co., Ltd. and sold under the trade name of Nipsil VN-3) | 49 |
| | 100 wt. % |

The clove oil and hydrous silicic acid were charged and kneaded together in a kneader for 30 minutes to obtain a putty-form product, which was then canned as the base agent. The base agent was found to be easily available from within the can with the use of a spatula.

(b) Setting agent

| | |
|---|---|
| Zinc oxide | 80.0 |
| Olive oil | 14.0 |
| Anhydrous silicic acid methylated on the surface and having a mean particle size of 16 millimicrons (manufactured by Nippon Aerosil, K. K. and sold under the trade name of Aerosil R-972) | 5.2 |
| Zinc acetate | 0.8 |
| | 100.0 wt. % |

The zinc oxide, olive oil, anhydrous silicic acid and zinc acetate were charged and kneaded together in a kneader for 1 hour to obtain a putty-form product, which was then canned as the setting agent. The setting agent was found to be very easily available from within the can by means of a spatula.

Equal amounts of the base and setting agents were placed on a mixing pad with a spatula, on which they could be mixed together within a short time of 20 seconds. A setting time of 4 minutes 15 seconds gave a set product of suitable workability, the abrasion loss (or depth) of which was 80 microns, and showed a 20 to 30% decrease as compared with Comparison Examples 1 and 2. This indicated that the set product had improved durability.

EXAMPLE 2

(a) Base agent

| | |
|---|---|
| Clove oil | 64.0 |
| Anhydrous silicic acid methylated on the surface and having a mean particle size of 16 millimicrons (manufactured by Nippon Aerosil, K. K. and sold under the trade name of Aerosil R-972) | 35.5 |
| Glacial acetic acid | 0.5 |
| | 100.0 wt. % |

The clove oil, anhydrous silicic acid and glacial acetic acid were charged and kneaded together in a kneader for 40 minutes to obtain a putty-form product, which was canned as the base agent. That agent was found to be very easily available from within the can by means of a spatula.

(b) Setting agent

| | |
|---|---|
| Zinc oxide | 81.5 |
| Rosin | 5.0 |
| Camellia oil | 10.0 |
| Titanium oxide (of the anatase type and 300 millimicrons in mean particle size) | 1.5 |
| Barium sulfate (having a mean particle size 1800 millimicrons) | 2.0 |
| | 100.0 wt. % |

The camellia oil and rosin were charged in a kneader, and were molten by heating at 100° C. for 20 minutes, followed by well-stirring. The zinc oxide, titanium oxide and barium sulfate were then added to and kneaded with the obtained product for 15 minutes. The resulting product was cast into a can, and was cooled off to obtain a putty-form setting agent, which was found to be very easily available from within the can by means of a spatula.

Equal amounts of the base and setting agents were placed on a mixing pad with a spatula, on which they could be mixed together within a short time of 25 seconds. A setting time of 4 minutes 20 seconds gave a set product of suitable workability, the abrasion loss (or depth) of which was 68 microns, and showed a 30 to 40% decrease as compared with Comparison Examples 1 and 2. This indicated that the set product had improved durability.

EXAMPLE 3

(a) Base agent

| | |
|---|---|
| Clove oil | 41.5 |
| Hydrogenated rosin | 36.0 |
| Hydrous silicic acid having a mean particle size of 30 millimicrons (manufactured by Tokuyama Soda, K. K. and sold under the trade name of Tokuseal GU) | 17.5 |
| Anhydrous silicic acid having a mean particle size of 7 millimicrons (manufactured by Nippon Aerosil, K. K. and sold under the trade name of Aerosil 300) | 4.5 |
| Glacial acetic acid | 0.5 |
| | 100.0 wt. % |

The clove oil and hydrogenated rosin were charged in a kneader, and were molten by heating at 110° C. for 40 minutes, followed by well-stirring. The hydrous and anhydrous silicic acids and glacial acetic acid were then added to the obtained product for 20-minute kneading. The thus kneaded product was cast into a can, and was cooled off to obtain a putty-form base agent, which was found to be very easily available from within the can by means of a spatula.

(b) Setting agent

| | |
|---|---|
| Zinc oxide | 89.2 |
| Olive oil | 7.0 |
| Castor oil | 3.0 |
| Hydrous silicic acid having a mean particle size of 30 millimicrons (manufactured by Mizusawa Kagaku, K. K. and sold under the | 0.8 |

-continued

| | |
|---|---|
| trade name of Silton R2) | |
| | 100.0 wt. % |

The zinc oxide, olive oil, castor oil and hydrous silicic acid were charged in a kneader for 1-hour kneading to obtain a putty-form product, which was then canned as the setting agent. That agent was found to be very easily available from within the can by means of a spatula.

Equal amounts of the base and setting agents were placed on a mixing pad with a spatula, on which they could be mixed together within a short time of 15 seconds. A setting time of 4 minutes 15 seconds gave a set product of suitable workability, the abrasion loss (or depth) of which was 75 microns, and showed a 21 to 38% decrease as compared with Comparison Examples 1 and 2. This indicated that the set product had improved durability.

EXAMPLE 4

(a) Base agent

| | |
|---|---|
| Clove oil | 50.0 |
| Rosin | 43.5 |
| Anhydrous silicic acid having a mean particle size of 40 millimicrons (manufactured by Nippon Aerosil, K. K. and sold under the trade name of Aerosil OX-50) | 3.2 |
| Anhydrous silicic acid having a mean particle size of 6 millimicrons (manufactured by Nippon Aerosil, K. K. and sold under the trade name of Aerosil 130) | 2.8 |
| Glacial acetic acid | 0.5 |
| | 100.0 wt. % |

The clove oil and rosin were charged in a kneader, and were molten by heating at 100° C. for 30 minutes, followed by well-stirring. The two anhydrous silicic acids and glacial acetic acid were then added to the obtained product for 15-minute kneading. The keanded product was cast into a can, and was cooled off to obtain a putty-form product as the setting agent, which was found to be very easily available from within the can by means of a spatula.

(b) Setting agent

| | |
|---|---|
| Zinc oxide | 72.5 |
| Camellia oil | 9.0 |
| Olive oil | 4.0 |
| Magnesium silicate having a mean particle size of 500 millimicrons | 8.0 |
| Hydrous silicic acid having a mean particle size of 15 millimicrons (manufactured by Nippon Silica, K. K. and sold under the trade name of Nipsil ER) | 6.5 |
| | 100.0 wt. % |

The zinc oxide, camellia oil, olive oil, magnesium silicate and hydrous silicic acid were charged and kneaded together in a kneader for 1-hour to obtain a putty-form product, which was then canned as the setting agent. That agent was found to be very easily available from within the can by means of a spatula.

Equal amounts of the base and setting agents were placed on a mixing pad with a spatula, on which they could be mixed together within a short time of 20 seconds. A setting time of 4 minutes 30 seconds gave a set product of suitable workability, the abrasion loss (or depth) of which was 78 microns, and showed a 18 to 35% decrease as compared with Comparison Examples 1 and 2. This indicated that the set product had improved durability.

EXAMPLE 5

(a) Base agent

| | |
|---|---|
| Clove oil | 45.0 |
| Rosin | 39.1 |
| Hydrous silicic acid having a mean particle size of 10 millimicrons (manufactured by Shionogi Seiyaku, K. K. and sold under the tradename of Carplex 67) | 7.5 |
| Hydrous silicic acid having a mean particle size of 8 millimicrons (manufactured by Nippon Silica, K. K. and sold under the trade name of Nipsil NS) | 8.0 |
| Glacial acetic acid | 0.4 |
| | 100.0 wt. % |

The clove oil and rosin were charged in a kneader, and were molten by heating at 100° C. for 30 minutes, followed by well-stirring. The two hydrous silicic acids and glacial acetic acid were then added to the obtained product for 20-minute kneading. The thus kneaded product was cast into a can, and was cooled off to obtain a putty-form base agent, which was found to be very easily available from within the can by means of a spatula.

(b) Setting agent

| | |
|---|---|
| Zinc oxide | 80.5 |
| Camellia oil | 6.0 |
| Peanut oil | 5.5 |
| Magnesium hydroxide having a mean particle size of 200 millimicrons | 4.5 |
| Hydrous silicic acid having a mean particle size of 12 millimicrons (manufactured by Nippon Aerosil, K. K. and sold under the trade name of Aerosil 200) | 2.5 |
| Aluminium silicate having a mean particle size of 35 millimicrons | 1.0 |
| | 100.0 wt. % |

The zinc oxide, camellia oil, peanut oil, magnesium hydroxide, hydrous silicic acid and aluminium silicate were charged and kneaded together in a kneader for 1-hour to obtain a putty-form product, which was then canned as the setting agent. That agent was found to be very easily available from within the can by means of a spatula.

Equal amounts of the base and setting agents were placed on a mixing pad with a spatula, on which they could be mixed together within a short time of 20 seconds. A setting time of 4 minutes 20 seconds gave a set product of suitable workability, the abrasion loss (or depth) of which was 84 microns, and showed a 12 to 30% decrease as compared with Comparison Examples 1 and 2. This indicated that the set product had improved durability.

COMPARISON EXAMPLE 1

(a) Base agent (liquid)

| | |
|---|---|
| Clove oil | 100% by weight |

The clove oil liquid was put into a liquid bottle as the base agent.

(b) Setting agent (powder)

| Zinc oxide | 99.2 |
|---|---|
| Zinc acetate | 0.8 |
| | 100.0 wt. % |

The zinc oxide and zinc acetate were mixed together for 30 minutes in a mixer, and the obtained powdery mixture was put into a powder bottle.

With the use of a pipet, 0.2 ml of the liquid base agent were poured onto a mixing pad, while 1 g of the powdery setting agent was placed on the same pad, and was divided into about three equal portions. The first portion of the setting agent was mixed with 0.2 ml of the liquid base agent for 20 seconds, the second portion was added to and mixed with the thus obtained mixture for 20 seconds, and the final portion was added to and mixed with the thus obtained product for 30 seconds. Thus, a total mixing time of as long as 70 seconds was needed to complete mixing. The setting time was 4 minutes 30 seconds, but a time period left for manipulation was short due to the extended mixing time. The abrasion loss (or depth) was 95 microns.

COMPARISON EXAMPLE 2

(a) Base agent (paste)

| Clove oil | 53.5 |
|---|---|
| Rosin | 46.0 |
| Glacial acetic acid | 0.5 |
| | 100.0 wt. % |

The clove oil and rosin were charged in a kneader, and were molten by heating at 110° C. for 40 minutes, followed by well-stirring. The glacial acetic acid was then added to and kneaded with the thus obtained product for 20 minutes, and the resulting product was put into a tube, and was cooled off to obtain a pasty base agent.

(b) Setting agent (paste)

| Zinc oxide | 88.0 |
|---|---|
| Olive oil | 7.0 |
| Castor oil | 5.0 |
| | 100.0 wt. % |

The zinc oxide, olive oil and castor oil were charged and kneaded together in a kneader for 1 hour to obtain a pasty kneaded product, which was then put into a tube.

Equal amounts of the base and setting agents forced out of the respective tubes were placed on a mixing pad, on which they could be mixed within a mixing time of 30 seconds in a relatively easy manner. A setting time of 4 minutes 40 seconds gave a set product of suitable warkability. The abrasion loss (or depth) was as large as 120 microns, indicating that the set product was soft.

TABLE 1

| | Example 1 | Example 2 | Example 3 | Example 4 | Example 5 | Comparative 1 | Comparative 2 |
|---|---|---|---|---|---|---|---|
| Sample availability | ⊚ | ⊚ | ⊚ | ⊚ | ⊚ | X | ○ |
| Time needed to finish mixing (sec) | 20 | 25 | 15 | 20 | 20 | 70 | 30 |
| Setting Time (min:sec) | 4:15 | 4:20 | 4:15 | 4:30 | 4:20 | 4:30 | 4:40 |
| Abrasion loss (depth in micron) | 80 | 68 | 75 | 78 | 84 | 95 | 120 |
| Sample leakage | | | | | | | X |

Availability:
⊚ - very easy
○ - easy
X - difficulty
Abrasion Loss:
Abrasion Tester
A nylon toothbrush (of 0.25 mm in diameter and having 790 furs planted thereon per square centimeter) was reciprocated 10,000 times on each sample (of 10.0 mm in diameter and 5.0 mm in height) a 48g/cm$^2$ in load and 50 mm in distance. The abrason loss was then expressed in terms of a mean abrasion depth in micron.
Leakage of Sample out of Container: After the container is permitted to stand for 30 days at 60° C., the leakage of sample out of container is visually observed.
⊚ - No leakage found
○ - No substantial leakage found
X - Considerably leakage found

EXAMPLES 6 TO 14

In Examples 6 to 14, the base and setting agent compositions were formulated in the proportions as specified in Table 2 according to the procedures of Examples 1 to 5. Testings were carried out in accordance with Examples 1 to 5 for the measurement of availability, time needed to finish mixing, setting time, abrasion loss and leakage of each sample out of each container. In consequence, it was ascertained that Examples 6 to 14 showed the same excellent performance as did Examples 1 to 5, as set forth in Tables 2 and 3.

TABLE 2

| | | Example 6 | Example 7 | Example 8 | Example 9 | Example 10 |
|---|---|---|---|---|---|---|
| Base Agent Composition | Clove oil | 60.0 | 60.0 | 52.0 | 57.8 | 58.0 |
| | Silicic Acid | Hydrous silicic acid (30 mμ) 39.5 | Hydrous silicic acid (300 mμ) 39.5 | Anhydrous silicic acid (30 mμ) 27.5 | Anhydrous silicic acid (7 mμ) 5.0 Hydrous silicic acid (10 mμ) | Anhydrous silicic acid (30 mμ) 42.0 |

TABLE 2-continued

|  |  |  |  |  | 5.0 |  |
|---|---|---|---|---|---|---|
| Additives | Acetic acid 0.5 | Acetic acid 0.5 | Rosin 20.0 | Hydrogenated Rosin 32.0 | — |
|  |  |  | Acetic acid 0.5 | Acetic acid 0.2 |  |
| Setting Agent Composition | Zinc Oxide Inorganic Filler | 75.5 Aluminium oxide (200 mµ) 9.0 | 75.0 Anhydrous silicic acid (16 mµ) 6.0 Calcium oxide (300 mµ) 3.0 | 74.0 Anhydrous silicic acid (40 mµ) 6.5 Hydrous silicic acid (16 mµ) 2.0 Zirconium oxide (500 mµ) 2.0 | 79.0 Magnesium Oxide (300 mµ) 3.0 Aluminium hydroxide (1500 mµ) 5.0 | 82.0 Calcium hydroxide (400 mµ) 8.0 |
| Additives |  | Olive oil 14.5 Zinc acetate 1.0 | Olive oil 16.0 | Camellia oil 15.0 Zinc acetate 0.5 | Camellia oil 6.0 Olive oil 7.0 | Olive oil 5.0 Castor oil 4.0 Zinc acetate 1.0 |

|  |  |  | Example 11 | Example 12 | Example 13 | Example 14 |
|---|---|---|---|---|---|---|
| Base Agent Composition | Clove oil Silicic Acid | 66.0 Anhydrous silicic acid (16 mµ) 33.5 | 59.47 Hydrous silicic acid (1500 mµ) 40.5 | 38.0 Anhydrous silicic acid (40 mµ) 3.0 Hydrous silicic acid (40 mµ) 3.0 | 50.5 Hydrous silicic acid (16 mµ) 48.8 |
| Additives |  | Glacial acetic acid 0.5 | Yellow pigment 0.03 | Rosin 55.0 Acetic acid 1.0 | Acetic acid 0.5 Speamint 0.2 |
| Setting Agent Composition | Zinc Oxide Inorganic Filler | 88.5 Calcium Silicate (16 mµ) 2.0 | 78.0 Zirconium silicate (1800 mµ) 14.0 | 83.97 Anydrous silicic acid (300 mµ) 1.0 Hydrous silicic acid (300 mµ) 3.0 | 82.0 Titanium oxide (1800 mµ) 4.0 Calcium hydroxide (300 mµ) 2.0 Zirconium silicate (1000 mµ) 2.0 |
| Additives |  | Olive oil 9.5 | Camellia oil 5.0 Peanut oil 3.0 | Olive oil 12.0 Red pigment 0.03 | Olive oil 10.0 |

The bracketed figure means the mean particle size.

TABLE 3

|  | Example 6 | Example 7 | Example 8 | Example 9 | Example 10 | Example 11 | Example 12 | Example 13 | Example 14 |
|---|---|---|---|---|---|---|---|---|---|
| Sample availability | ◎ | ◎ | ◎ | ◎ | ◎ | ◎ | ◎ | ◎ | ◎ |
| Time needed to finish mixing (sec) | 20 | 25 | 20 | 20 | 25 | 20 | 25 | 30 | 30 |
| Setting time (min:sec) | 4:30 | 4:30 | 4:15 | 4:45 | 4:45 | 4:15 | 4:30 | 4:15 | 4:30 |
| Abrasion loss (Depth in micron) | 66 | 68 | 80 | 81 | 75 | 70 | 77 | 85 | 65 |
| Sample leakage | ◎ | ◎ | ◎ | ◎ | ◎ | ◎ | ◎ | ◎ | ◎ |

As will be understood from Tables 1 to 3, the comparison of the examples with the comparison examples indicates that, by making putty the base and setting agents of the zinc oxide eugenol cement by adding respectively the finely divided silicic acid and inorganic filler, the material is so easily available in a suitable amount, rapid mixing and dispersion of both agents causes that the time needed to finish mixing is only ½ to ¼ of that of the conventional products, any leakage of the material out of the container does not occur at all during storage, and the material undergoes no substantial change in the setting time due to storage, maintains constantly stable quality, and provides a set product having improved abrasion resistance, as expressed in terms of an abrasion loss (or depth) of 20 to 30% decrease. Thus, the temporary sealing material can be so easily handled regardless of skillfulness, and has improved abrasion resistance with no fear of deformation or disengagement. With the temporary sealing and cementing material of the present invention, it is possible to shorten the chair time in dentistry and maintain clearer treatment environment. Thus, efficient and comfortable daignosis and treatment activities as well as effective treatment are expected for all the persons engaged in dentistry such as dentists, dental hygienists and assistants, whereas patients can receive comfortable and effective treatment.

What is claimed is:

1. A dental zinc oxide eugenol cement composition comprising in combination:
    A. a putty-form base agent composition in which 5.0 to 50.0% by weight of silicic acid having a mean particle size of 2 to 2000 millimicrons are contained in an eugenol-containing base agent composition, and
    B. a putty-form setting agent composition in which 0.5 to 15.0% by weight of an inorganic filler material having a solubility of up to 0.2 g per 100 ml of water at 20° C. are contained in a zinc oxide-containing setting agent composition.

2. A cement composition as defined in claim 1, in which said inorganic filler material has a mean particle size of 2 to 2000 millimicrons.

* * * * *